United States Patent
Pathak et al.

(10) Patent No.: US 9,382,579 B2
(45) Date of Patent: Jul. 5, 2016

(54) DNA/NANOPARTICLE COMPLEX ENHANCED RADIO FREQUENCY TRANSPONDER: STRUCTURE OF MARK FOR DETECTING HYBRIDIZATION STATE AND AUTHENTICATING AND TRACKING ARTICLES, METHOD OF PREPARING THE SAME, AND METHOD OF AUTHENTICATING THE SAME

(71) Applicants: Bogdan Amaru Pathak, Toledo, OH (US); Walter John Keller, III, Bridgeville, PA (US)

(72) Inventors: Bogdan Amaru Pathak, Toledo, OH (US); Walter John Keller, III, Bridgeville, PA (US)

(73) Assignee: NOKOMIS, INC., Charleroi, PA (US)

( * ) Notice: Subject to any disclaimer, the term of this patent is extended or adjusted under 35 U.S.C. 154(b) by 0 days.

(21) Appl. No.: 14/208,728

(22) Filed: Mar. 13, 2014

(65) Prior Publication Data
US 2014/0271365 A1 Sep. 18, 2014

Related U.S. Application Data

(60) Provisional application No. 61/851,784, filed on Mar. 13, 2013, provisional application No. 61/788,465, filed on Mar. 15, 2013.

(51) Int. Cl.
| | |
|---|---|
| *C12M 1/34* | (2006.01) |
| *C12M 1/00* | (2006.01) |
| *C12Q 1/68* | (2006.01) |
| *H01J 3/14* | (2006.01) |
| *H04B 7/04* | (2006.01) |
| *H04Q 5/22* | (2006.01) |
| *G01N 33/566* | (2006.01) |
| *G01N 22/00* | (2006.01) |

(52) U.S. Cl.
CPC .............. *C12Q 1/6825* (2013.01); *G01N 22/00* (2013.01)

(58) Field of Classification Search
CPC ......... C12Q 1/68; C12Q 1/6825; G01N 22/00
USPC ..................... 435/6.1, 283.1, 287.2; 436/501; 977/773; 340/10.1; 250/9.1; 424/9.1
See application file for complete search history.

(56) References Cited

U.S. PATENT DOCUMENTS

| | | | |
|---|---|---|---|
| 6,361,944 B1 * | 3/2002 | Mirkin | C12Q 1/6837 435/6.11 |
| 6,373,387 B1 | 4/2002 | Qiu et al. | |
| 6,696,953 B2 | 2/2004 | Qiu et al. | |
| 6,835,926 B2 * | 12/2004 | Weitekamp | G01R 29/12 250/225 |
| 7,515,094 B2 | 4/2009 | Keller, III | |
| 7,653,982 B2 | 2/2010 | Chopra et al. | |
| 7,874,489 B2 | 1/2011 | Mercolino | |
| 7,943,394 B2 * | 5/2011 | Flandre | G01N 27/221 422/82.01 |
| 8,063,813 B1 | 11/2011 | Keller | |
| 8,220,716 B2 | 7/2012 | Mercolino | |
| 2002/0048822 A1 | 4/2002 | Rittenburg et al. | |
| 2005/0112610 A1 | 5/2005 | Lee et al. | |
| 2006/0019373 A1 * | 1/2006 | Kahlman | G01N 27/745 435/287.2 |
| 2006/0154300 A1 * | 7/2006 | Park | G01N 33/54373 435/7.1 |
| 2009/0286250 A1 | 11/2009 | Hayward et al. | |
| 2010/0073135 A1 * | 3/2010 | Potyrailo | G01D 21/00 340/10.1 |
| 2010/0123453 A1 | 5/2010 | Pauly et al. | |
| 2010/0190270 A1 * | 7/2010 | Piazza | C12Q 1/6816 436/524 |
| 2010/0285985 A1 | 11/2010 | Liang et al. | |
| 2012/0223403 A1 | 9/2012 | Keller et al. | |
| 2012/0226463 A1 | 9/2012 | Keller et al. | |
| 2012/0269728 A1 * | 10/2012 | Jen | B01D 15/3804 424/9.1 |

OTHER PUBLICATIONS

Chien et al, DNA detection using a radio frequency biosensor with gold nanoparticles, 2008, Frontiers in Bioscience, 13, 4756-4764.*
J. H. Chien, C. H. Chang, Y. F. Hsieh, D. S. Lee, L. S. Kuo, C. H. Yang, C. R. Yang, W. P. Chou and P. H. Chen; A Dual-Mode Radio Frequency DNA Sensor; Department of Mechanical Engineering, National Taiwan University, Taiwan 106 R.O.C., Department of Air-Conditioning and Refrigeration, National Taipei University of Technology, Taipei, Taiwan 106 R.O.C.; Department of Mechatronic Technology, National Taiwan Normal University, Taipei, Taiwan, 106 R.O.C.

* cited by examiner

*Primary Examiner* — Narayan Bhat
(74) *Attorney, Agent, or Firm* — James Ray and Assocs

(57) ABSTRACT

An apparatus comprises an antenna pattern precursor, wherein the antenna pattern precursor includes a plurality of sensitive regions; and electromagnetically functionalized DNA/nanoparticle complex(es) that individualize the ability to transition between the precursor antenna electrical and resonant frequency characteristics, and activated antenna electrical and resonant frequency characteristics through DNA hybridization of the specific sequences contained in the electromagnetically functionalized DNA/nanoparticle complex(es).

1 Claim, 8 Drawing Sheets

DNA/NANOPARTICLE COMPLEX ENHANCED RADIO FREQUENCY TRANSPONDER: STRUCTURE OF MARK FOR DETECTING HYBRIDIZATION STATE AND AUTHENTICATING AND TRACKING ARTICLES, METHOD OF PREPARING THE SAME, AND METHOD OF AUTHENTICATING THE SAME

CROSS-REFERENCE TO RELATED APPLICATIONS

This application is related to and claims priority from U.S. Provisional Patent Application Ser. No. 61/851,784 filed on Mar. 13, 2013 and U.S. Provisional Patent Application Ser. No. 61/788,465 filed Mar. 15, 2013; this application is also closely related to Utility patent application Ser. No. 13/410,797 filed on Mar. 2, 2012, titled "System and Method for Physically Detecting Counterfeit Electronics" and now published as U.S. publication number 2012-0226463 published Sep. 6, 2012, whose teachings are incorporated into this document by reference thereto.

These applications are being assigned to the assignee of the present invention and the disclosures of these applications are hereby incorporated by reference thereto.

FIELD OF THE INVENTION

The present invention is in the technical field of security marking, authentication, and biological diagnostics. More particularly, the present invention is in the technical field of electrically enabled transponders comprising functionalized DNA and individualized antennas. The individual aspects of the antennas and the hybridization state of the functionalized DNA, which is causally related to its sequence, are able to be decoded using an extremely sensitive radio-frequency detector. This enables wireless authentication of articles, which in this application are exemplified by an integrated circuit, as well as biological diagnostics.

REFERENCE TO A SEQUENCE LISTING, A TABLE, OR A COMPUTER PROGRAM LISTING COMPACT DISC APPENDIX

N/A

BACKGROUND OF THE INVENTION

There exists a critical need to have a unique and difficult to replicate marking system that can be individualized to specific articles to enable users and brokers to determine the authenticity of articles prior to utilization. (E.g., integration into a circuit board or larger systems; acceptance as authentically manufactured; etc.). This capability would allow for rejection of counterfeits through a series of progressively tighter controls, depending on the criticality of the article and the effect its failure would have on a system or the acceptance by a consumer, ensuring that only authentic parts would be integrated or purchased.

There further exists a need to more inexpensively and rapidly identify unique segments of DNA for disease detection and prevention, pathogen diagnosis, and a wide variety of other or related applications.

Related Applications for Mark Structure
    Integrated hybrid electronic article surveillance marker, U.S. Pat. No. 6,373,387, Apr. 16, 2002
    Integrated hybrid electronic article surveillance marker, U.S. Pat. No. 6,696,953, Feb. 24, 2004
    Product Authentication, U.S. Pat. No. 7,874,489, Jan. 25, 2011
    Product Authentication, U.S. Pat. No. 8,220,716, Jul. 17, 2012
    Marking of Products with Electroactive Compounds, Ser. No. 09/404,414, Sep. 23, 1999

Related Applications for Mark Preparation
    System and Method for marking textiles with nucleic acids, Ser. No. 10/825,968, Apr. 15, 2004
    Incorporating Soluble Security Markers into Cyanoacrylate solutions, Ser. No. 12/465,450, May 13, 2009
    Method and Systems for the Generation of plurality of security markers and the detection thereof, Ser. No. 12/690,799, Jan. 20, 2010
    Individually Unique Hybrid Printed Antennae for Chipless RFID Applications, U.S. Pat. No. 7,653,982 B2, Feb. 22, 2010

Related Applications for Mark Reader
    System and method for physically detecting counterfeit electronics, Ser. No. 13/410,797, Mar. 2, 2012
    Active improvised explosive device (IED) electronic signature detection, U.S. Pat. No. 8,063,813, Nov. 22, 2011
    Integrated circuit with electromagnetic energy anomaly detection and processing, Ser. No. 13/410,909, Mar. 2, 2012
    Advanced electromagnetic location of electronic equipment, U.S. Pat. No. 7,515,094, Apr. 7, 2009
    ADVANCE MANUFACTURING MONITORING AND DIAGNOSTIC TOOL, Ser. No. 12/551,635, Sep. 1, 2009

SUMMARY OF THE INVENTION

This invention teaches a DNA/NanoParticle Enhanced Radio Frequency Transponder, hereinafter also referred to as "DNA/NP ERFT", typically in the form of a tag or mark applied to an article that will re-emit a unique RF signature when in the presence of a low level RF field, and re-emit one or more different unique RF signatures when combined with a key solution or sequence of key solutions and then exposed to a low level RF field. The described DNA/NP ERFT determines the lineage of an article and act as a key tool in the fight against counterfeits.

The mark authentication apparatus utilizes a sensitive radiofrequency detection tool. The method of authentication measures RF signatures at sensitivities unavailable in other state of the art devices.

As described below, The DNA/NP ERFT comprising a RF tag with unique re-emission characteristics taught under this invention provides a primary indicator of genuine articles that supplements and complements other counterfeit detection modalities taught in "System and method for physically detecting counterfeit electronics" and "Integrated circuit with electromagnetic energy anomaly detection and processing" listed above.

For the purposes of this invention, the term individualized indicates an element or the totality of a marker or structure that is associated with a datum or conceptual element of the article to which it is attached. For example, a particular aspect of the marker could code for the date of manufacture, another the serial number, a third the color, etc. The particular aspect could be realized in the form of an antenna trace width, tag geometry, or DNA sequence depending upon the structure that the word individualized is modifying.

This invention teaches reradiating RF tags and their method of manufacture which may be individualized for many purposes including authentication, which is the example embodiment described in this invention. The tags comprise individualized antennas physically attached to a substrate in conjunction with one or more Electromagnetically Functionalized NanoParticle/DNA complexes (EMFNP/DNACs) which form electrical components and subsequently alter the emissions of the individualized antennas, forming a DNA/NP ERFT. The sensitivity of the customized antennas to changes in electrical changes due to changes in physical structure introduced by hybridizing the marker DNA-encoded electrical components provides a key-based authentication scheme. The sequence(s) of DNA, the physical layout of the sequences, and the antenna patterning provide an almost infinite number of unique markings.

The changes in the re-radiated spectrum, such as frequency shift, phase shift, relationship between emissions, or spectral shape of the emissions acquired from these DNA/NP ERFTs in both the unhybridized and hybridized forms form a strong basis for authentication. The relationship formed by the re-radiated spectrum of the base antenna, the re-radiated spectrum of the antenna with unhybridized EMFNP/DNAC elements (i.e., the DNA/NP ERFT prior to forensic authentication), and the re-radiated spectrum of the antenna with correctly hybridized EMFNP/DNA elements (i.e., the DNA/NP ERFT after authentication with the complementary key EMFNP/DNAC) can only be achieved on that article by matching the sequence of the marker EMFNP/DNAC to its complementary EMFNP/DNAC. Thus, if the part does not have the appropriate EMFNP/DNAC sequence, the antenna it was tagged with, or if either the EMFNP/DNAC sequence or antenna itself has changed—having been degraded by remarking or previous use—the authentication system will identify the tag as not matching the signature profile of an article on record.

DNA/NP ERFTs are not RFID tags. RFID tags are designed to encode a specific digital signal that does not interconnect their structure to the data which they convey; rather, their data is stored in a structure and then transmitted through a common antenna design, or one that utilizes metallic complexes that do not contain biological molecules. The majority of RFID tag innovations stem from their ability to be fixed on different articles or to be encoded with a digital sequence that is then decoded by standard digital means. In contrast, DNA/NP ERFTs encode their information through the antenna's unique structures complemented by the sequence of DNA bases, which are then decoded through hybridization and the resulting variation in their resonant frequency.

The manufacturing processes for both said unique printed antennas and said electromagnetically functionalized nanoparticle (EMFNP)/DNA hybrid sequences have been previously described as have various article marking processes; however, the marking process envisioned in this invention integrates the antenna and EMFNP/DNA deposition process into a single step.

OBJECTS OF THE INVENTION

It is, therefore, one of the primary objects of the present invention to provide unique, individualized antennas that are printed onto the articles to harvest and reradiate specific bands of RF energy.

Another object of the present invention is to provide ElectroMagnetically Functionalized NanoParticles (EMFNPs) coupled to a plurality of DNA sequences that, when functionalized by said EMFNPs, affect electrical components of which they are a part, and in turn the frequency responses, of the unique antennas, forming a DNA/NP ERFT.

Yet another object of the present invention is to provide for multiple levels of marking and signature verification, and verification at several tiers (steps) of the article integration process.

A further object of the present invention is to provide that the DNA/NP ERFTs radiate in different spectral bands, allowing multiple articles to be screened simultaneously, without having to remove them from secondary packaging.

Another of the primary objects of the present disclosure is to teach an embodiment of the elements and variable structure of the DNA/NP ERFTs and the novel and non-obvious aspects of the underlying concept.

Yet a further object of the present invention is to provide intensive authentication though coding of the DNA sequences, which coupled with the individualized antenna designs, trace individual components directly to the manufacturer, lot, and even a specific article.

An additional object of the present invention is to provide multiple DNA sequences that can predictably be combined independently, at the time of marking, making the variety of markers virtually endless without having to as zealously guard the individual marker components.

A further object of the present invention is to provide a modality for a built-in detector/receiver/authentication device (as previously disclosed in "System and method for physically detecting counterfeit electronics" and "Integrated circuit with electromagnetic energy anomaly detection and processing") within any larger system that can be programmed to alert if a marked article is illicitly replaced without appropriate measures.

Yet another object of the present invention is to provide an increased capability for a small hand-held automatic detector that can be used to screen entire sets of articles automatically.

An additional object of the present invention is to provide a marker whose response is structurally stable over temperature, time, etc. due to the inherent characteristics of DNA.

A further object of the present invention is to disclose a technique to associate a specific article with a slightly different antenna geometry, trace, or element that will ultimately provide a slightly offset emissions signature from a former or future marker.

Yet a further object of the present invention is to provide a unique, constantly changing set of antenna patterns that can by itself be used as an effective tool to track and authenticate articles.

An additional object of the present invention is to provide a first tier of marker uniqueness through the antenna's unique geometry, trace width, or elements.

Another object of the present invention is to provide means to ensure that the reproduction of the structure of each antenna element would require reasonable effort and resources.

Yet another object of the present invention is to provide process for printing the entire mark with an inkjet or other proven photolithography technique.

A further object of the present invention is to provide a customized mix of DNA sequences and DNA coated geometries in each marker Yet a further object of the present invention is to provide a great variety of both DNA sequences as well as a mix of individual DNA enhanced elements in each marker that cannot be easily duplicated or predicted.

An additional object of the present invention is to detect the hybridization of the DNA-sequence dependent tag using electromagnetic emissions.

Another object of the present invention is to provide a virtually unlimited number of unique combinations of DNA sequences embedded in the unique EMFNP/marker DNA based electrical elements as a means of authentication.

A further object of the present invention is to provide a second tier of marker uniqueness through the use of EMFNP/marker DNA uniqueness.

Another object of the present invention is to provide a authentication modality that is able to penetrate the secondary packaging of a typical article.

Yet another object of the present invention is to provide a means of authentication that does not require DNA amplifying techniques when verifying the parts at a second, more thorough screening as would be typical for other DNA-based approaches.

A further object of the present invention is to provide an authentication mechanism wherein only a small amount of the complementary EMFNP/DNA (on the order of several µL) will be needed to properly hybridize with the verification DNA, leading to the expected change in RF signature.

Yet a further object of the present invention is to provide a marker that is persistent after physical handling and temperature excursions;

An additional object of the present invention is to provide a marker that is obviously destroyed after surface modification by sanding and blacktop recoat, sandblasting, and mechanical lapping.

Another object of the present invention is to provide a unique antenna structure that will resonate and reradiate at a different frequency when the EMFNP/DNA elements are absent.

Yet another object of the present invention is to provide a cost effective and secure marker.

A further object of the present invention is to provide a means of data decoding utilizing the sequential addition of complementary EMFNP/DNA sequences.

Another object of the present invention is to provide a means for detecting the melting of hybridized DNA by capturing and analyzing the emissions of customized antenna patterns loaded with EMFNP/DNA elements.

Yet another object of the present invention is to use the melting temperature of hybridized EMFNP/DNA elements to infer the specific sequences of DNA bases.

A further object of the present invention is to provide an additional verification of the security marker and an additional authentication modality through the correlation between EMFNP/DNA melting temperature and the change in emitted signature.

In addition to the several objects and advantages of the present invention which have been described with some degree of specificity above, various other objects and advantages of the invention will become more readily apparent to those persons who are skilled in the relevant art, particularly, when such description is taken in conjunction with the attached drawing Figures and with the appended claims.

BRIEF DESCRIPTION OF THE VARIOUS EMBODIMENTS OF THE INVENTION

Figure 1:
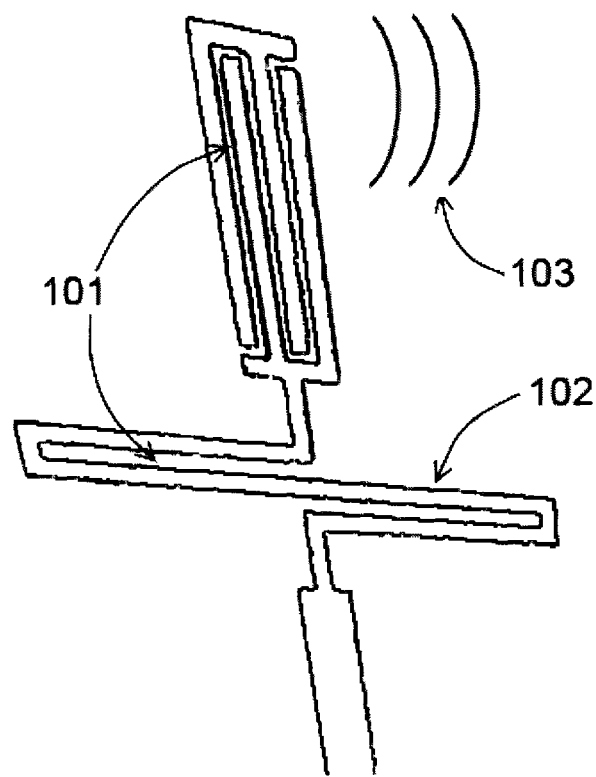
FIG. 1 is an embodiment of individualized antennas that are printed onto the articles to harvest and reradiate specific bands of RF energy.

Prior to proceeding to the more detailed description of the present invention, it should be noted that, for the sake of clarity and understanding, identical components which have identical functions have been identified with identical reference numerals throughout the several views illustrated in the drawing figures.

It is to be understood that the definition of an inauthentic or substandard article is one that in the case of an electronic device applies to but is not limited to work-alike electronic device, used electronic devices which have been removed from existing assemblies and sold as new and genuine parts, electronic devices which have been remarked to misrepresent their model/part number, manufacturer, cage code, date and/or lot code, reliability level, inspection, level of testing, or performance specification, electronic devices which do not conform to Original Component Manufacturer design, model, and/or performance standards, electronic devices which have been deliberately or unintentionally modified, electronic devices which have been deliberately modified to pose a security threat, and electronic devices which have been deliberately and/or intentionally modified for a malicious purpose with the intent to deceive as to the intended function.

Referring now to FIG. 1, the Customizable Radiating Antenna Unit (102) is without limitation a conductive ink, paste, or metalized pattern that is placed on each article that may be tied to its manufacturing lot, date, location, and even serial number within the lot. Sensitive Gap Region (101) is without limitation a region within Customizable Radiating Antenna Unit (102) that when loaded with hybridized and/or unhybridized EMFNP/DNA complexes changes the induced emissions (103). The Customizable Radiating Antenna Unit can be manually customizable or configured to achieve uniqueness, or customized or configured through computerized automatic semi-randomization of a base antenna pattern's elements' length, width, location and angle with respect to an adjoining conductive antenna element. The objective of the customization is to more fully or with more certainty achieve uniqueness in the antenna's frequency vs. dB response or resonance.

The term customizable used herein is meant as the ability to apply a means of modifying the antenna structure, manually or automatically, to further differentiate its electromagnetic RF response from the average, typical antenna unit. It can be considered to be a configurable physical pattern resulting in a different RF response from the typical customized antenna unit.

Figure 2:
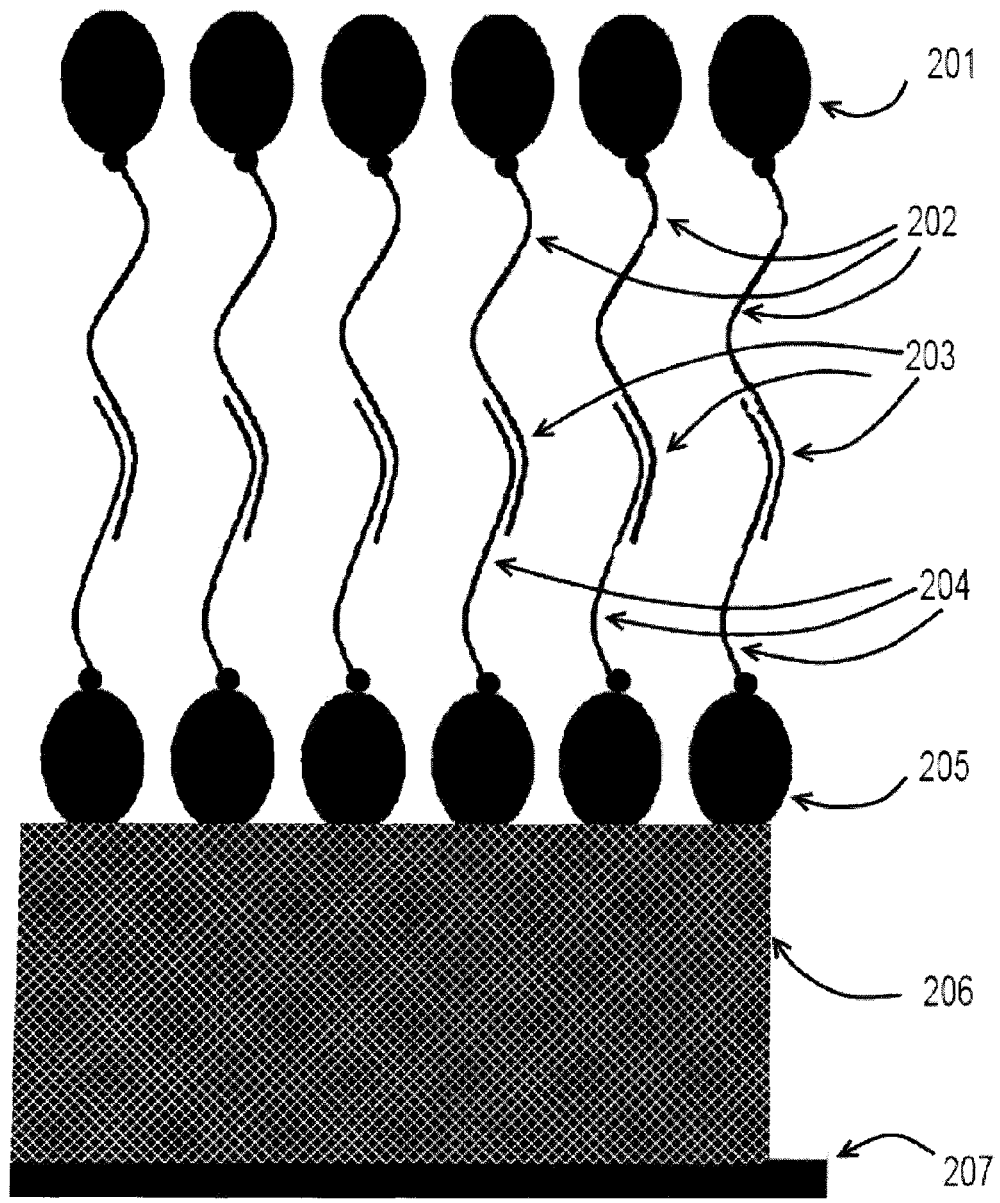
FIG. 2 is a conceptual illustration of EMFNPs coupled with DNA sequences that, when hybridized, generate electrically reactive elements, and in turn, affect the emissions of the individualized antennas (without limitation) at resonance and sub-resonance frequencies.

FIG. 2 is a conceptual illustration of the structure of a hybridized EMFNP/DNA based electrical element. It shows marker DNA (204) coupled with base EMFNPs (205) on its 5' end. The marker DNA (204) is fixed to the article to be marked (207) without limitation by 3-aminopropyltrimethoxysilane, cyanoacrylate, or simply by Van der Waals forces inherent to the EMFNPs (206). The marker DNA (204) can be hybridized directly with the complementary DNA strand (202) which is coupled with additional EMFNP (201) on said complementary DNA strands 5' end. The hybridization occurs at the hybridization region (203).

Figure 3:
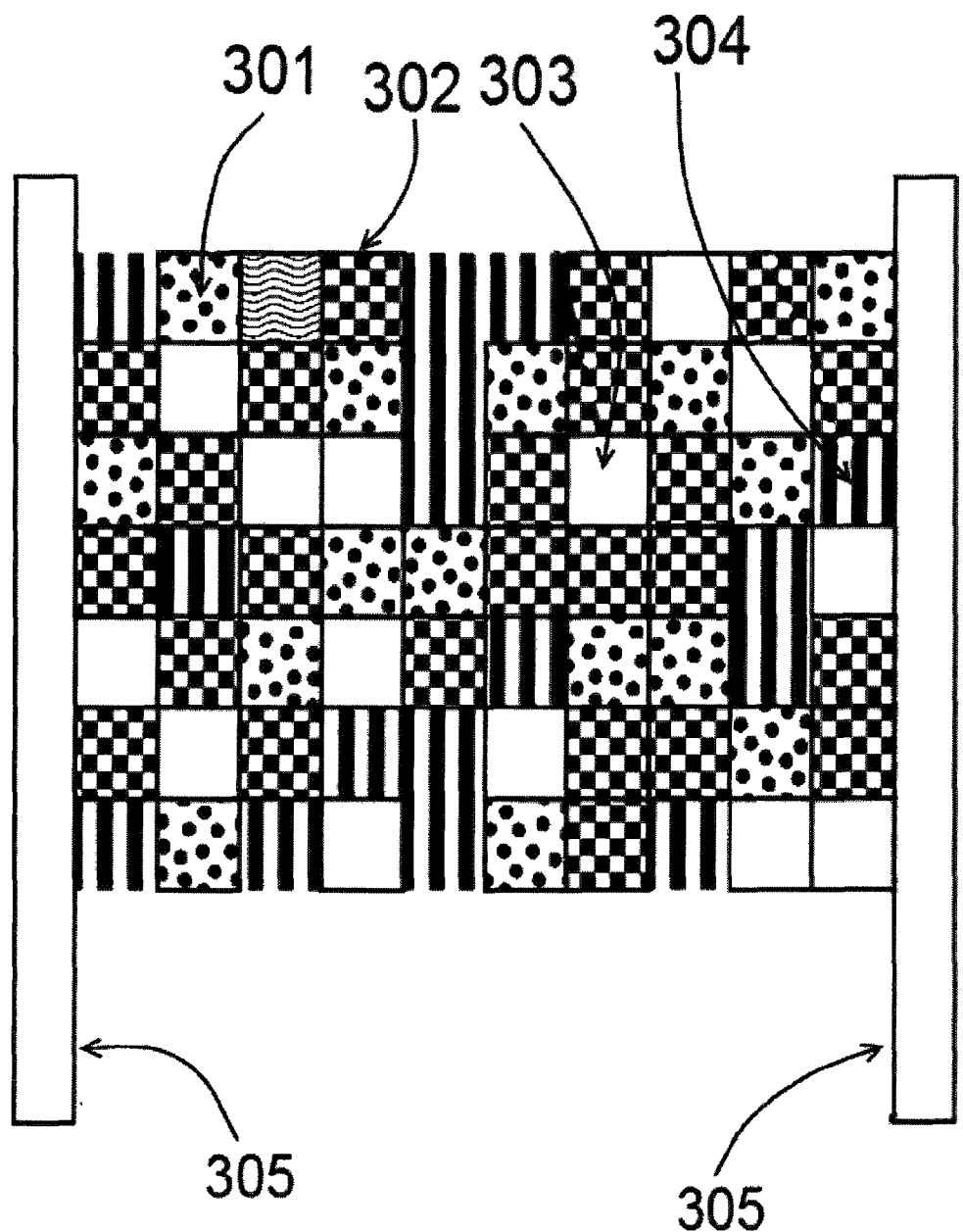
FIG. 3 is an example illustration of a Sensitive Gap Region (101) and the patterning of individual EMFNP/DNA regions that could be utilized to generate additional security elements within a marker. The patterns described are without limitation.

FIG. 3 shows EMFNP/DNAC element geometry segregated by sequence; EMFNP/DNAC with Sequence A (301), EMFNP/DNAC with Sequence B (302), EMFNP/DNAC with Sequence C (303), and EMFNP/DNAC with Sequence D (304) generate a unique geometry that requires that the appropriate complementary EMFNP/DNAC sequences are utilized for verification simultaneously. Unless all complementary sequences are present, the electrical element formed by EMFNP/DNAC with Sequences A-D (301-304) will not affect the sensitive gap region in between the antenna elements (305) in the expected manner. In addition, by the sequential addition of complementary EMFNP/DNA sequences, changes in the emitted signature of the Customized Radiating Antenna Pattern (102) is capable of communicating additional encoded information stored in the EMFNP/DNA element geometry.

Still referring to FIG. 3, as previously described in FIG. 1, the EMFNP/marker DNA enhancement fixed to the article via (206) as shown in FIG. 2 would typically be placed in the sensitive gap region (101) comprising the areas between the digits or meanders of the customized antenna pattern (102) as previously illustrated in FIG. 1.

Figure 4:
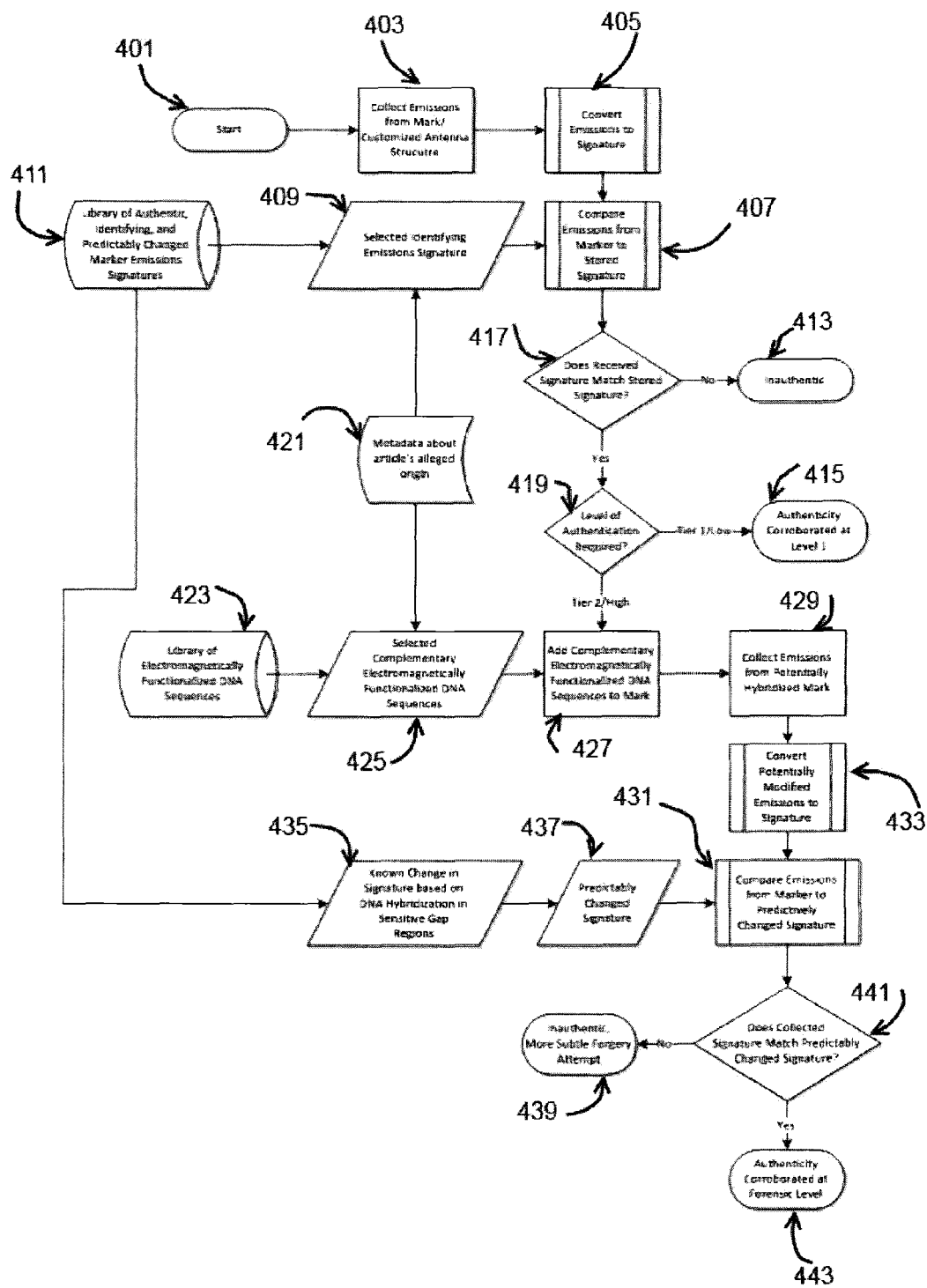
FIG. 4 describes an algorithmic process with the object of discerning the authenticity of an article utilizing the present invention and demonstrates two tiers of authentication. Once hybridized, the DNA/NP ERFT can be reverted to its unhybridized state through heating as illustrated in FIG. 5; this reversion provides another level of authentication.
Figure 5:
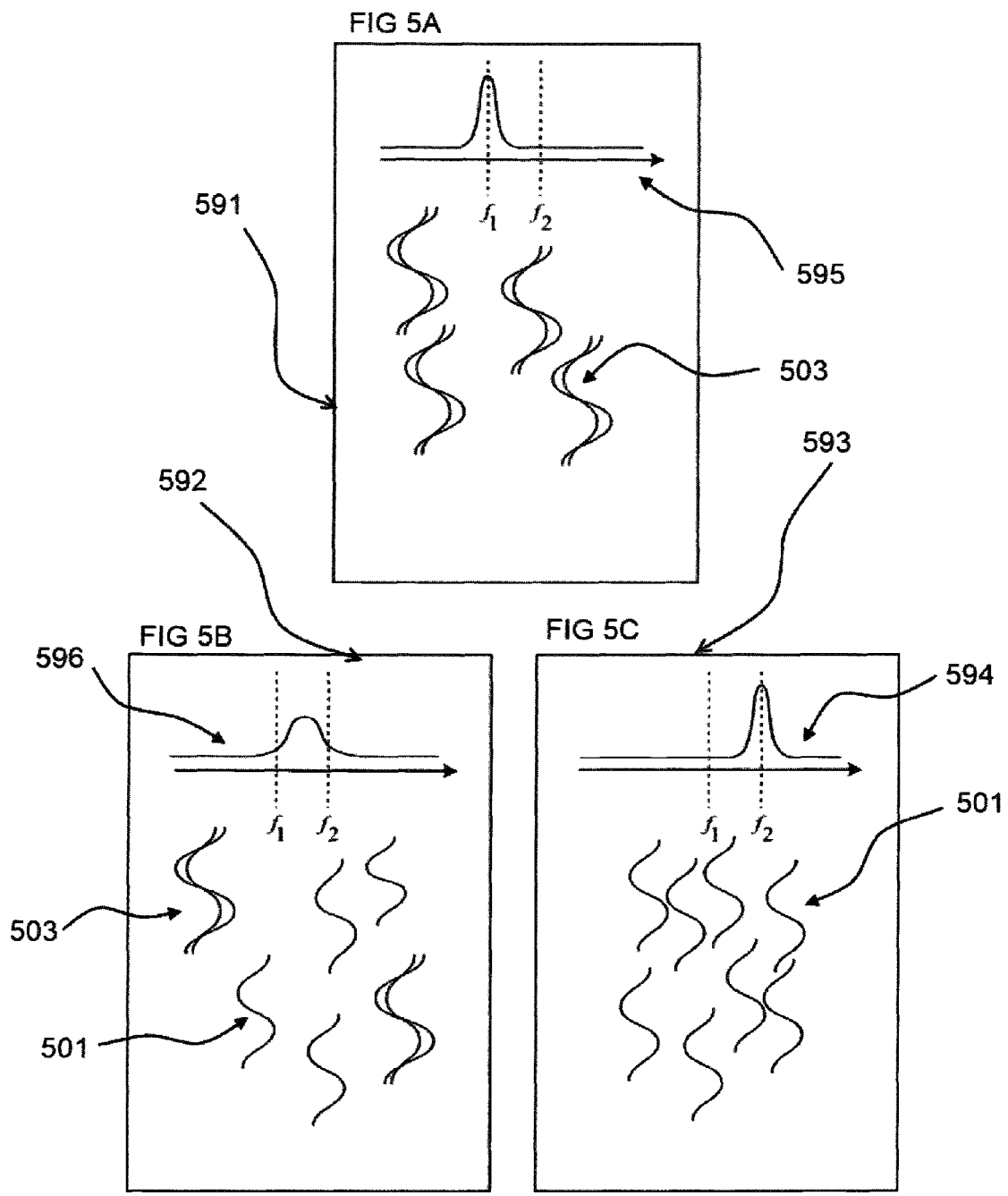
FIG. 5A, FIG. 5B, and FIG. 5C are conceptual illustrations of the correlations between the changes in a captured signature and EMFNP/DNA sequence melting levels based upon the specific ratios of DNA bases. The correlation between the melting temperature and the change in emitted signature provides an additional security marker.

Referring now to the invention in more detail, in FIG. 4 is shown, without loss of generality, an algorithmic process as an embodiment of means to accomplish the objects of this invention. Still referring to FIG. 4, there is shown the starting step 401 wherein the marked article enters the algorithm process for authentication, along with article origin metadata 421 as provided by an external source. Still referring to FIG. 4, in collection step 403, a receiver such as without loss of generality disclosed in US Pub 20120226463 published Sep. 6, 2012 and titled "System and method for physically detecting counterfeit electronics", and whose teachings are incorporated into this document by reference thereto, collects analog emissions from an DNA/NP ERFT that has been applied to the article such as without loss of generality in the first embodiment of the invention disclosed previously; next, conversion step 405, which without loss of generality may be incorporated into the receiver, converts said analog emissions into a digital signature using a series of algorithms. Still referring to FIG. 4, said article origin metadata 421 is utilized to select the expected emissions signature data from emissions signature library 411 through a preliminary signature selection step resulting in selected preliminary identifying emissions signature 409; said selected preliminary identifying emissions signature 409 is then compared with the digital signature that is the output of conversion step 405 in tier 1 comparison step 407.

A preferred optimized means of reading the Customizable Radiating Antenna Unit using minimal space and in a noise-free environment is to implement the apparatus for detection and/or identification of counterfeit and/or substandard electronic devices described in Ser. No. 14/199,687 in March 2014 as a "METHOD AND APPARATUS FOR DETECTION AND IDENTIFICATION OF COUNTERFEIT AND SUBSTANDARD ELECTRONICS". This apparatus is also well suited for processing a reel or array of prepared candidate tags to be tested in an efficient, mechanized, automated environment.

Still referring to FIG. 4, said tier 1 comparison step 407 answers tier 1 signature matching query 417; if preliminary signature matching query 417 results in a negative match the article is deemed inauthentic 413 and the algorithm terminates; if instead tier 1 signature matching query 417 results in a positive match, processing continues with authenticity level desired query 419. If authenticity level desired query 419 returns tier 1/low, then the algorithm terminates with the article authenticity being corroborated at tier 1 415.

Still referring to FIG. 4 at authenticity level desired query 419, if the output from authenticity level desired query 419 is tier 2/high, then the algorithm continues with further processes. The process then requires the addition of selected complementary EMFNP/DNAC sequence(s) 425, which have been without loss of generality selected or produced from a library of EMFNP/DNAC sequences 423 based on article origin metadata 421, in addition step 427. Following addition step 427, a receiver such as without loss of generality disclosed in US Pub 20120226463 published Sep. 6, 2012 and titled "System and method for physically detecting counterfeit electronics", and whose teachings are incorporated into this document by reference thereto, collects tier 2 analog emissions from said DNA/NP ERFT that has been applied to said article in tier 2 collection step 429. Next, tier 2 conversion step 433, which without loss of generality may be incorporated into said receiver, converts said analog emissions into a digital signature using a series of algorithms. Still referring to FIG. 4, said article origin metadata 421 is utilized to generate different expected emissions signature data based upon hybridization-based signature changes 435 due to hybridization of the marker EMFNP/DNA complex based electrical elements and preliminary identifying emissions signature 409 from emissions signature library 411 through a forensic signature generation step resulting in selected forensic identifying emissions signature 437; said selected forensic identifying emissions signature 437 is then compared with the digital signature that is the output of tier 2 conversion step 433 in tier 2 comparison step 431.

Continuing to refer to FIG. 4, said tier 2 comparison step 431 answers forensic signature matching query 441; if forensic signature matching query 441 results in a negative match the article is deemed more subtly inauthentic 439 and the algorithm terminates; if instead forensic signature matching query 441 results in a positive match, then the algorithm terminates with the article being corroborated at forensic authenticity level 439.

Now referring to FIG. 2, FIG. 5A, FIG. 5B, FIG. 5C, and FIG. 6, hybridized response correlation 591 schematically shows hybridized EMFNP/DNA complexes 503 with the corresponding conceptual hybridized overall DNA/NP ERFT frequency response 595. This response is correlated with fully hybridized temperature/% hybridization region 611 on FIG. 6, where % Hybridization 605 is on the vertical axis and temperature 607 is on the horizontal axis. As the temperature is increased, hybridized EMFNP/DNA complexes 503 melt and convert to unhybridized EMFNP/DNA complexes 501. The associated melting temperature 613 corresponds to the ratios of A-T and C-G DNA base pairs in hybridization region 203, which are specific to authentic marker and corresponding authentic marker trace 602 and can be distinguished from an inauthentic marker and corresponding inauthentic marker trace 601. In 50% hybridized response correlation 592, there is an equal ratio of hybridized EMFNP/DNA complexes 503 and unhybridized EMFNP/DNA complexes 501, which detunes the response of the DNA/NP EFRT, resulting in melting temperature overall DNA/NP ERFT frequency response 596. As the temperature continues to increase, all hybridized EMFNP/DNA complexes 503 melt and form unhybridized EMFNP/DNA complexes 501, resulting in fully melted overall DNA/NP ERFT frequency response 594 which corresponds to fully melted temperature/% hybridization region 615. The correlation between fully melted overall DNA/NP ERFT frequency response 594 and unhybridized EMFNP/DNA complexes 501 contained in original DNA/NP ERFT is shown in original DNA/NP ERFT response correlation 594.

Figure 6:
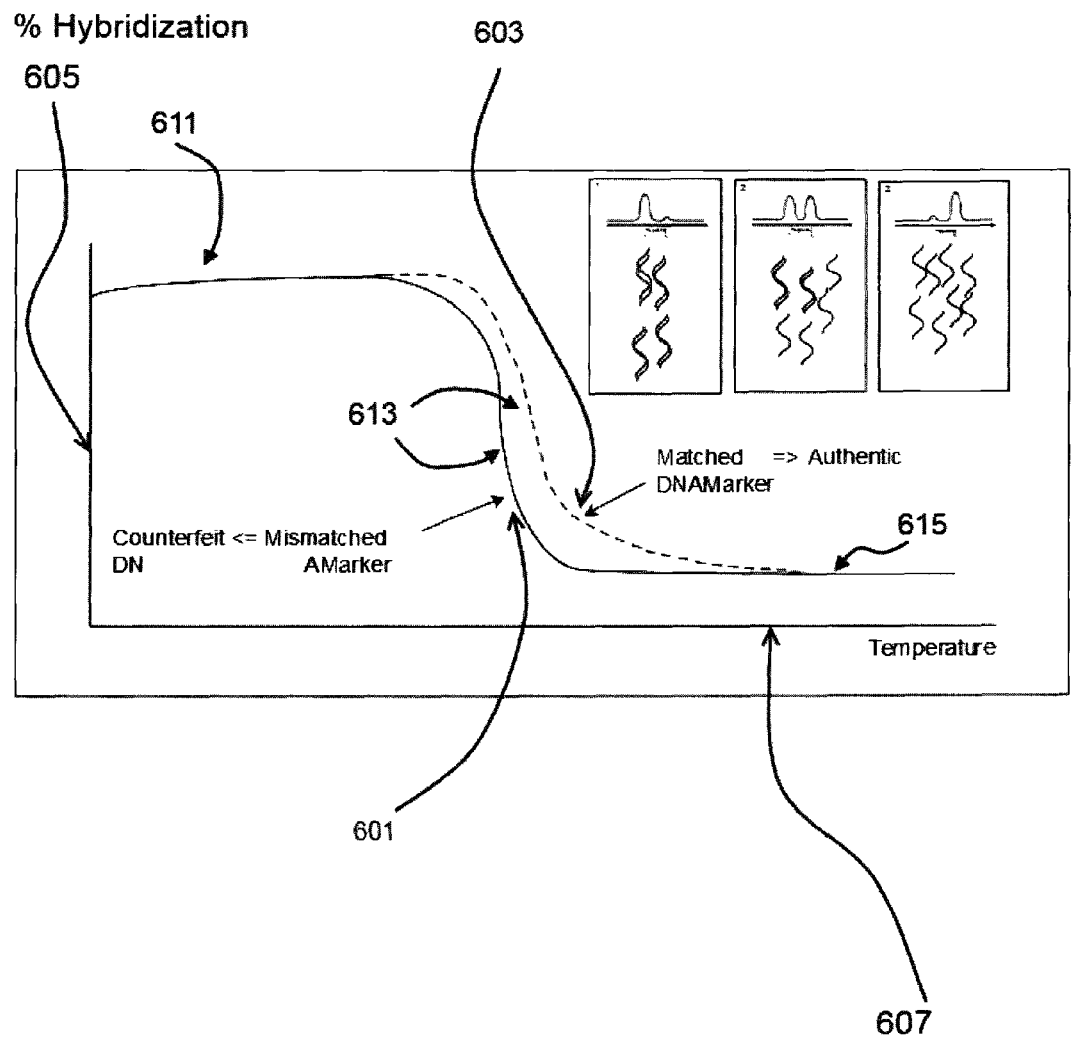
FIG. 6 is a graph showing the counterfeit and authentic tag frequency vs. temperature response of a specific tag antenna region resulting when the effects illustrated in FIG. 5 are achieved.

Still referring to FIG. 6, the function of the tag as it is heated slowly with a high resolution temperature change is to elucidate that the ratio of base pairs in the DNA base sequence is different between the counterfeit and authentic tags causing a difference in melt temperature.

Figure 7:
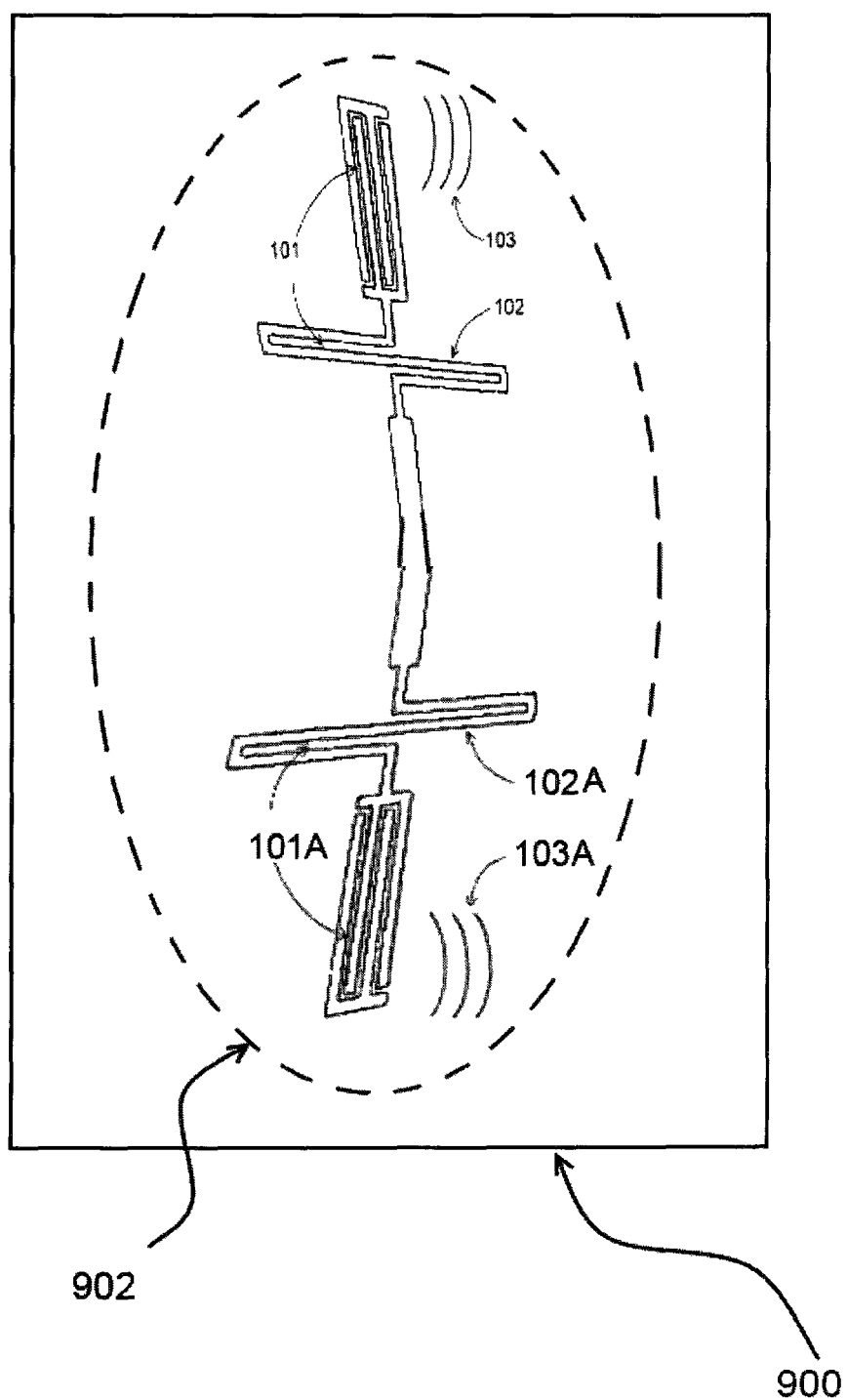
FIG. 7 depicts one exemplary tag.

Referencing FIGS. 1, 2, and 7, the tag 900 with loaded antenna region 902 has been printed to form a preprinted default Selectable Resonant Antenna Structure. Said loaded antenna region 902 contains a plurality of Sensitive Gap Regions (101 and 101A) between its elements that are receptive to marker EMFNP/DNA complexes comprising marker DNA (204) coupled to base EMFNPs (205), which have been loaded into an individualized number of said Sensitive Gap Regions (101 and 101A). By adding a key solution of complementary EMFNP/DNA complexes comprising complementary DNA strand (202) and additional EMFNP (201) in said Sensitive Gap Regions (101 and 101A) within antenna regions 102 and 102A, the marker DNA (204) will hybridize with the complementary DNA strand (202) forming and change the electrical properties of the regions and overall antenna frequency responses 103 and 103A are modified. Adding a key solution containing non-complementary EMFNP/DNA complexes will result in no hybridization, and will not form a hybridized DMFNP/DNA based electrical element as shown in FIG. 2 and no change in overall antenna frequency responses 103 and 103A. This accordingly provides a basis for authentication. The antenna will be completed with one or preferably multiple such marker EMFNP/DNAC Sequences to produce a finished tag 950 (shown in FIG. 8). Therefore, the finished tags 950 will each have a unique response determined by the antenna geometry and presence of different EMFNP/DNAC Sequences bound to different regions between segments of the Selectable Resonant Antenna Structure. The term key solution used herein is used to convey the combinations derived from the coding elements of the bases in the DNA applied to complementary EMFNP/DNA complexes, which act as a physical key to a lock. Thus only a specific DNA 'key' will bind, and a key solution is the solution of DNA in a liquid medium which may or may not bind depending on the sequences potentially matching and contained therein.

Reference is now made, to FIGS. 1-8, wherein there is shown an apparatus, generally designated as transponder tag 950, for generating a plurality of DNA modified electromagnetic responses to a series of electromagnetic stimuli 962, typically initiated by an external transponder tag reader 960, said stimuli sent by said transponder tag reader's transmitter 966 and responses received by transponder tag reader's receiver 968.

Figure 8:
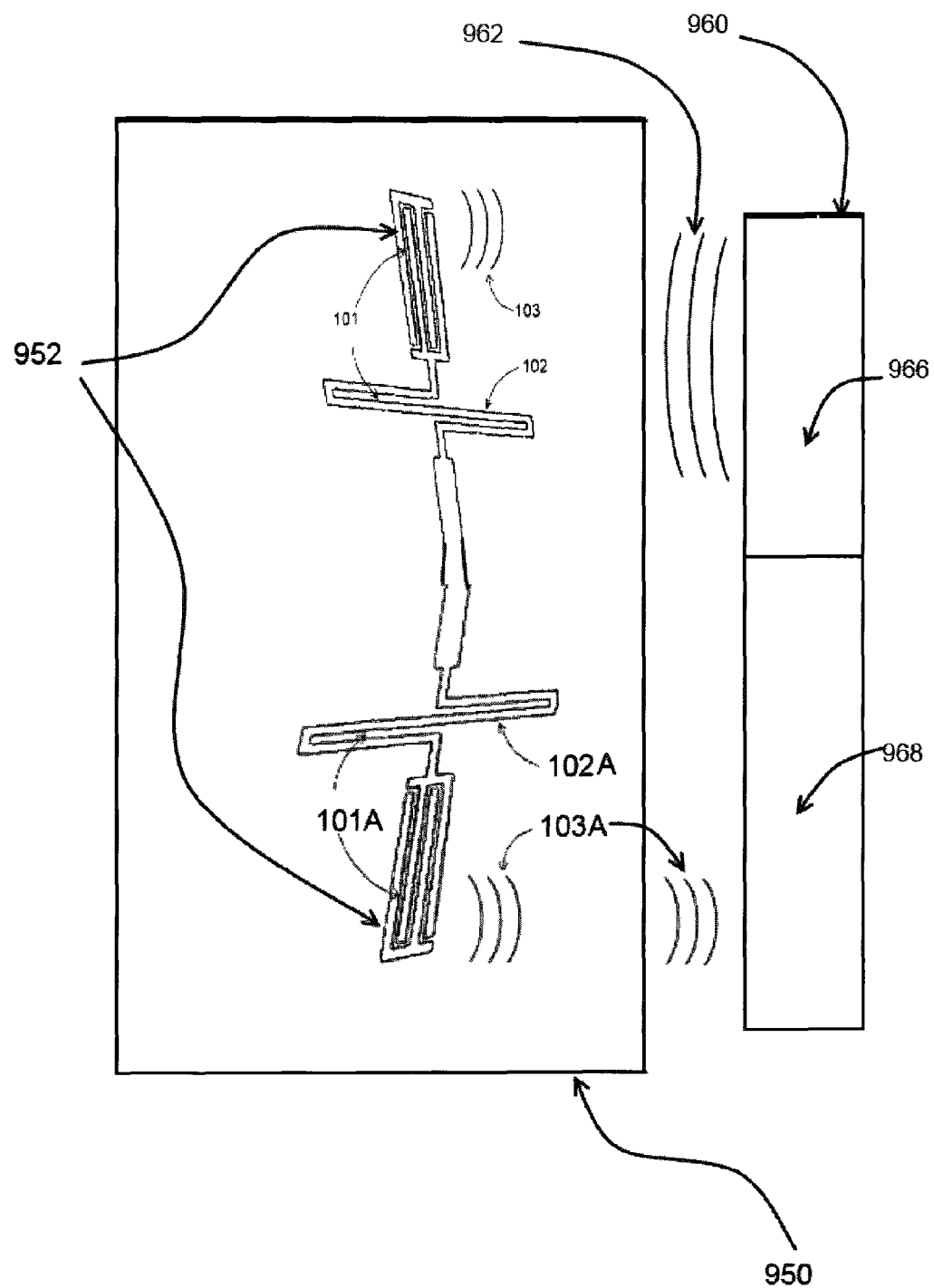
FIG. 8 depicts one exemplary loaded transponder with a relatively complex antenna geometry and/or overall total antenna length in the process of having its emissions collected.

Now in a particular reference to FIG. 8, said transponder tag 950 comprises of two essential elements, Customizable Radiating Antenna System, generally designated as 952, and DNA modified electromagnetically responding antenna elements, generally designated as 101 and 102 as one responding element and 101A and 102A as a second responding element, that are operatively coupled to Customizable Radiating Antenna System 952 on the DNA electromagnetically modified tag 950. The completed Customizable Radiating Antenna System 952 separately contributes to the overall completed tag 950 response. The tag 950 receives required signals as a series of electromagnetic stimuli 962 from the transponder tag reader's transmitter 966 into the tag 950's DNA-modified antenna circuits 101, 102, 101A, and 102A, and responds with electromagnetic energy 103 and 103A which is captured by the receiver 968, preferably in a radiofrequency (RF) range from about 10 kilohertz (KHz) to about 300 gigahertz (GHZ).

The Selectable Resonant Antenna Structure

The Selectable Resonant Antenna Structure (902) is typically a mass-produced precursor to a finished antenna product. The word precursor used herein is meant to apply to a discrete intermediate recently manufactured physical antenna unit which exists in this form temporarily before being subsequently enhanced for further RF electromagnetic response specificity or uniqueness. Thus, the Selectable Resonant Antenna Structure is a printed set of wire segments, which can be subsequently processed to provide a plurality of uniquely receptive locations for unique EMFNP/DNAC sequences which modify the final antenna electrical characteristics.

In some embodiments, the Selectable Resonant Antenna Structure features the bulk of the antenna pattern. That is, in the interest of providing an economic Selectable Resonant Antenna Structure that can be mass-produced and then specifically tailored to a number of different final responses, it is desired that the Selectable Resonant Antenna Structure provides many sensitive DNA sites which can be loaded with specifically chosen DNA segments. For example, the Selectable Resonant Antenna Structure can provide 15 sites, but these 15 sites could be each be populated by $4^n$ NP/DNACs., where n is the number of bases in the DNA sequence. In many embodiments, the final DNA/NP ERFT combinations derived from the Selectable Resonant Antenna Structure will be 100 or more.

The Selectable Resonant Antenna Structure can be created as a plurality of disconnected and connected wire segments that have been printed via an analog printing process. Thus, the Selectable Resonant Antenna Structure provides wire segments that can be modified or augmented during a subsequent step, such as through digitally controlled inkjet printing, in order to produce the finished antenna. Generally, the number of disconnected and connected wire segments that can be provided in the Selectable Resonant Antenna Structure can range from two or greater to about 2000. In an exemplary embodiment, the number of disconnected and connected wire segments is from about 2 to about 20.

The Selectable Resonant Antenna Structure may have an overall geometry of any shape and/or pattern, and is not limited to the rectangular configurations as shown in FIG. 8. For example, the overall shape of the Selectable Resonant Antenna Structure may be polygonal or non-polygonal, symmetrical or non-symmetrical, and angular and/or round. Likewise, the disconnected segments may be printed in random configurations that can be specifically connected in different patterns in the subsequent digital printing step. Moreover, the gaps created by the disconnected segments are not limited to those as shown in FIG. 1. Instead, the number, spacing, and size of gaps created on a single Selectable Resonant Antenna Structure can vary, and can be regular or not, as desired. For example, the gaps can be located anywhere on the Selectable Resonant Antenna Structure, and may be located at random or at regularly spaced intervals. The gaps can be of any length or width, and the size of the gaps created by the disconnected segments on the Selectable Resonant Antenna Structure may or may not be uniform.

As desired, the Selectable Resonant Antenna Structures may be printed on any suitable substrate. For example, the substrate can be paper, glass art paper, bond paper, paperboard, Kraft paper, cardboard, semi-synthetic paper or plastic sheets, such as polyester or polyethylene sheets, and the like. These various substrates can be provided in their natural state, such as uncoated paper, or they can be provided in modified forms, such as coated or treated papers or cardboard, printed papers or cardboard, and the like. Further, the Selectable Resonant Antenna Structures can be printed one to a sheet, such as where the Selectable Resonant Antenna Structure is being printed onto a packaging material, or they can be printed as a plurality of Selectable Resonant Antenna Structures on a single sheet, such as where the Selectable Resonant Antenna Structures are printed onto a roll of paper, onto labels, or onto a sheet that will sub subsequently separated into multiple pieces.

The widths and lengths of the preprinted disconnected segments and interconnects may range from about 0.1 mm to about 10 mm for width, and from about 0.1 mm to about 35 m for length. Moreover, the widths of the preprinted disconnected segments and interconnects may differ, so that the width of the preprinted disconnected segments are thicker than that of the interconnects, or vice versa. Naturally, the lengths of preprinted disconnected segments and interconnects may also differ.

Additionally, the widths and/or lengths of the preprinted disconnected segments and/or the interconnects of a single finished antenna may vary. Therefore, an exemplary antenna may consist of preprinted disconnected segments and/or interconnects of various widths and/or lengths.

Optionally, additional processing steps, such as any of overcoating, drying and rinsing, alone or in combination, may follow the printing steps.

Examples

Printing the Selectable Resonant Antenna Structure

An Selectable Resonant Antenna Structure (with 1 mm gaps) with a footprint of approximately 4 cm.times.4 cm square, consisting of conductive elements, with a width of 1 mm lines, and 0.5 mm space between adjacent lines and a total virtual length of 33 m (and virtual resonant frequency of 300-3000 Mhz can be printed using a photolithographic process onto a substrate or using inkjet technology.

Although the present invention has been shown in terms of the apparatus and method for detection and/or identification of counterfeit and/or substandard items, it will be apparent to those skilled in the art, that the present invention may be applied to electronic devices, for example such as circuit boards and assemblies including circuit boards.

Thus, the present invention has been described in such full, clear, concise and exact terms as to enable any person skilled in the art to which it pertains to make and use the same. It will be understood that variations, modifications, equivalents and substitutions for components of the specifically described embodiments of the invention may be made by those skilled in the art without departing from the spirit and scope of the invention as set forth in the appended claims.

We claim:

1. An apparatus configured for a detection of DNA sequence(s), said apparatus comprising;
  (a) a radiating antenna unit precursor comprising:
    (i) a substrate,
    (ii) a plurality of disconnected conductive wire segments attached to and disposed substantially parallel to a surface of said substrate,
    (iii) a plurality of interconnects on said surface configured to interconnect at least two of said plurality of disconnected conductive wire segments,
    (iv) a plurality of gap regions, each spanning a distance between two conductive wire segments from said plurality of wire segments,
    (v) a plurality of different marker electromagnetically functionalized nanoparticle (EMFNP)/DNA sequences disposed within some of said gap regions, each marker EMFNP/DNA sequence comprising marker DNAs coupled to base EMFNPs, and
    (vi) said plurality of marker EMFNP/DNA sequences defining a radio frequency (RF) response from said conductive wire elements of said radiating antenna unit, said RF response determined by a geometry of said radiating antenna unit and a presence of different marker EMFNP/DNAC sequences bound to different regions between said conductive wire segments of said radiating antenna unit;
  (b) a separate RF analyzer unit disposed at a distance from said radiating antenna unit and configured to determine said RF response of said radiating antenna unit, said RF analyzer unit comprising: an RF transmitter, an RF receiver, and an RF signal analysis section;
    (i) said RF transmitter configured to transmit a plurality of frequencies toward said radiating antenna unit,
    (ii) said RF receiver configured to receive said RF response from said radiating antenna unit at said plurality of frequencies transmitted by said RF transmitter section toward said radiating antenna unit,
    (iii) said RF receiver configured to receive an RF response above 300 Mhz from said radiating antenna unit,
    (iv) said RF transmitter configured to transmit electromagnetic energy radiation towards said radiating antenna unit above 300 Mhz,
    (v) said RF transmitter configured to transmit electromagnetic energy radiation within a substantially continuous range of frequencies,
    (vi) said RF transmitter and said RF receiver configured to only transmit and receive electromagnetic energy radiation substantially at a same frequency simultaneously, and
    (vii) said RF signal analysis section configured to determine if a comparative response at a received frequency has been met;
  wherein a key solution containing complementary EMFNP/DNA sequences applied to said radiating antenna unit causes at least one EMFNP/DNA sequence within the key solution to hybridize with marker EMFNP/DNA sequence within said gap regions, and further causes change in electrical properties of said gap regions and a change in an overall RF response from said radiating antenna unit being received at said RF receiver; and wherein a key solution containing non-complementary EMFNP/DNA complexes applied to said radiating antenna unit will not hybridize with marker EMFNP/DNA sequences within said gap regions and will not change overall RF response from said radiating antenna unit.

\* \* \* \* \*